(12) United States Patent
Davis

(10) Patent No.: US 6,888,101 B2
(45) Date of Patent: May 3, 2005

(54) HEATER FOR OPTICAL GAS SENSORS, GAS SENSORS INCLUDING THE HEATER, AND METHODS

(75) Inventor: Raymond G Davis, Seattle, WA (US)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 10/160,566

(22) Filed: May 31, 2002

(65) Prior Publication Data

US 2003/0006223 A1 Jan. 9, 2003

Related U.S. Application Data

(60) Provisional application No. 60/294,831, filed on May 31, 2001.

(51) Int. Cl.[7] ............................. H05B 3/00; H05B 3/84
(52) U.S. Cl. ..................... 219/201; 219/522; 219/543; 600/529; 73/23.3; 73/31.05; 128/200.24
(58) Field of Search ................ 219/201, 522, 219/543, 203; 359/512; 250/338.1–342, 504 R, 352; 600/529, 537, 532; 73/23.2, 23.3, 25.05, 335.01, 31.05; 128/200.24, 201.15

(56) References Cited

U.S. PATENT DOCUMENTS 1,473,029 A * 11/1923 Faubert et al. .............. 219/203

1,791,254 A * 2/1931 Brockdorff .................. 359/512

(Continued)

FOREIGN PATENT DOCUMENTS

| JP | 1-134418 | * 5/1989 | .................. 219/522 |
| JP | 2-148287 | * 6/1990 | |

OTHER PUBLICATIONS

U.S. patent application Ser. No. 09/128,897, filed on Aug. 4, 1998.

International Search Report, dated Oct. 25, 2002.

*Primary Examiner*—John A. Jeffery
(74) *Attorney, Agent, or Firm*—TraskBritt

(57) ABSTRACT

A heater for a window of an optical gas sensor is provided. The heater may be positioned over a portion of the window or may form at least a portion of the window. Alternatively, the heater may be separate from the optical gas sensor and positionable (e.g., by a transducer) over the window either in contact therewith or in close proximity thereto. The heater may be substantially transparent to the relevant wavelengths of electromagnetic radiation that are used in optical (e.g., infrared or luminescence quenching) monitoring of respiratory gases, anesthetic agents, or the like. Alternatively, the heater may be configured so as to provide a substantially unobstructed optical pathway through the window. Optical gas sensors and complementary transducers that include the healer are also disclosed.

62 Claims, 4 Drawing Sheets

U.S. PATENT DOCUMENTS

| | | | | |
|---|---|---|---|---|
| 2,557,983 | A | * 6/1951 | Linder | 219/543 |
| 3,495,259 | A | * 2/1970 | Rocholl et al. | 219/543 |
| 3,514,581 | A | * 5/1970 | Rocholl et al. | 219/543 |
| 4,427,888 | A | * 1/1984 | Galvin | 250/331 |
| 4,459,470 | A | * 7/1984 | Shlichta et al. | 219/522 |
| 4,694,173 | A | 9/1987 | Wong | |
| 4,772,790 | A | 9/1988 | Aldridge | |
| 4,859,835 | A | * 8/1989 | Balderson | 219/543 |
| 4,952,783 | A | 8/1990 | Aufderheide et al. | |
| 4,970,376 | A | * 11/1990 | Mellor et al. | 219/543 |
| 5,022,045 | A | * 6/1991 | Elliott | 374/20 |
| 5,092,342 | A | 3/1992 | Hattendorff et al. | |
| 5,146,092 | A | * 9/1992 | Apperson et al. | 250/343 |
| 5,493,102 | A | 2/1996 | Takase et al. | |
| 5,545,897 | A | * 8/1996 | Jack | 250/339.13 |
| 5,557,704 | A | * 9/1996 | Dennis et al. | 392/480 |
| 5,565,985 | A | 10/1996 | Fishkin et al. | |
| 5,597,953 | A | 1/1997 | Usanov et al. | |
| 5,703,352 | A | * 12/1997 | Snoeren et al. | 250/208.1 |
| 5,756,991 | A | * 5/1998 | Risinger et al. | 250/252.1 |
| 5,793,044 | A | * 8/1998 | Mace et al. | 250/343 |
| 5,846,650 | A | 12/1998 | Ko et al. | |
| 5,973,301 | A | * 10/1999 | Inoue | 219/522 |
| 6,011,622 | A | * 1/2000 | Fishkin et al. | 356/339 |
| 6,095,986 | A | 8/2000 | Braig et al. | |
| 6,303,909 | B1 | 10/2001 | Fernando et al. | |
| 6,325,978 | B1 | 12/2001 | Labuda et al. | |
| 6,521,877 | B1 | * 2/2003 | Muller-Rissmann et al. | 250/201.1 |
| 2002/0098120 | A1 | 7/2002 | Blazewicz et al. | |
| 2003/0122081 | A1 | * 7/2003 | Herrera et al. | 250/341.6 |

* cited by examiner

HEATER FOR OPTICAL GAS SENSORS, GAS SENSORS INCLUDING THE HEATER, AND METHODS

CROSS-REFERENCE TO RELATED APPLICATION

Under the provisions of 35 U.S.C. § 119(e), this application claims the benefit of U.S. Provisional Application Ser. No. 60/294,831, filed on May 31, 2001.

BACKGROUND OF THE INVENTION

1. Field of the Invention

The present invention relates generally to apparatus for delivering energy to optical windows of diagnostic apparatus and, more specifically, to apparatus that heat optical windows of gas analysis apparatus. In particular, the present invention relates to heaters for use on optical windows of respiratory gas analysis apparatus that provide a substantially unobstructed optical pathway through such optical windows.

2. Background of Related Art

Various types of sensors that are configured to communicate with the airway of a patient to facilitate measurement of the amounts of substances, such as gases or vapors, in the respiration of the patient are well known in the art. Similarly, techniques are well known in the art by which the amount of various substances in the patient's respiration may be measured.

Mainstream sensors are typically configured to be connected at some point along the length of a breathing circuit. Thus, as the patient breathes, respiratory gases and vapors that are flowing into or out of the breathing circuit pass directly through a mainstream sensor. Accordingly, a substantial portion of the patient's respiratory gases may be included in the measurement obtained by the sensor.

In contrast, sidestream sensors, rather than being located such that respiratory gases pass directly through the sensor, typically include small bore (i.e., inner diameter) sampling lines, or conduits, that "tap" into a breathing circuit to communicate therewith at some point along the length thereof. These small bore sampling lines draw small samples of the patient's respiratory gases from the breathing circuit. The samples then are conveyed to a sensor (e.g., a cuvette) that is located remotely from the breathing circuit. Measurements are then obtained to determine the amounts of one or more substances that are present in the sample.

By way of example, respiratory sensors such as those described above may be used in determining the amounts of molecular oxygen ($O_2$), carbon dioxide ($CO_2$) and anesthetic agents, e.g., nitrous oxide ($N_2O$), that are present in the respiration of a patient. These gas analyses are useful in a variety of other medical procedures including, without limitation, monitoring of the condition of a patient in critical or intensive care, in heart stress tests of an individual as he or she exercises (typically on a treadmill), and in other tests for monitoring the physical condition of an individual, or the like.

An exemplary, conventional mainstream gas sensor comprises a so-called "airway adapter" that includes a cuvette and that is configured to be coupled into a breathing circuit. A cuvette of such an airway adapter includes a chamber with a pair of opposed, substantially axially aligned optical windows flanking a sample flow path through the airway adapter. The windows have a high transmittance for radiation in at least a portion of the electromagnetic spectrum while maintaining an airtight seal in the breathing circuit. For infrared gas analysis, the material from which the windows are formed transmits a portion of the spectrum of electromagnetic radiation that corresponds to the wavelength or wavelengths of infrared radiation.

One optical gas monitoring technique that has long been employed to facilitate the detection and monitoring of gases, such as $O_2$, $CO_2$, and $N_2O$ and other anesthetic agents, is infrared absorption. In infrared absorption techniques, infrared radiation of one or more wavelengths and of known intensity is directed into a stream of respiratory gases. The wavelength or wavelengths of such radiation are selected based upon the gas or gases being analyzed, each of which absorbs one or more specific wavelengths of radiation. The intensity of the radiation which passes through the stream of respiratory gases, typically referred to as "attenuated radiation," is measured and compared with the known intensity of the radiation that was directed into the stream. This comparison of intensities provides information about the amount of radiation of each wavelength that is absorbed by each analyzed gas. In turn, information is provided concerning the amount (i.e., the concentration or fraction) of each analyzed gas that is present in the patient's respiration.

When infrared-type gas sensors are used, the respiratory gases of an individual are typically channeled, by way of a nasal canula or endotracheal tube, along a breathing circuit to a cuvette in communication therewith. If the patient is unable to breathe on his or her own, a mechanical ventilation machine may be coupled to an opposite end of the breathing circuit. Respiratory gases are channeled along a defined sample flow path that passes through the cuvette, which provides an optical pathway between a source of infrared radiation and an infrared radiation detector. In some cuvettes, the source and detector may be detachably coupled to the cuvette.

Another known optical gas monitoring method is referred to as "luminescence quenching." Luminescence quenching has been used to measure the amount of oxygen and other gaseous or vaporized materials in respiratory samples and other gas and/or vapor mixtures. Typically, luminescence quenching requires the emission of excitation radiation from a source toward a luminescing material. The luminescing material has a luminescence chemistry, the luminescence of which may be quenched specifically by one or more types of gaseous or vaporized materials which may be measured (e.g., oxygen, an anesthetic agent, etc.). The excitation radiation to which the luminescing material is exposed causes the material to be excited and to emit electromagnetic radiation of a different wavelength than the excitation radiation. The presence of the one or more materials of interest quenches the luminescing material. Stated differently, if a luminescence quenching gas or vapor of interest is present, the amount of radiation emitted by the luminescing material will be reduced. The amount of radiation emitted by the luminescing material and the rate at which such radiation is quenched are measured by a detector and compared with the amount of radiation emitted by the luminescing material and the rate at which the luminescence of the luminescing material is quenched in the absence of the luminescence quenching gas or gases of interest. This comparison facilitates a determination of the amount of the one or more sensed, luminescence quenching gases (e.g., in the respiration of a patient) to which the luminescing material is exposed.

For instance, when luminescence quenching is used to measure the amount of oxygen in a respiratory sample, an appropriate luminescing material (i.e., at least one wavelength of the luminescence of which is quenched when exposed to oxygen) is first excited to luminescence. Upon exposure of the luminescing material to $O_2$, the luminescence thereof is quenched. The amount of quenching is indicative of the amount of oxygen present in a gas mixture to which the luminescing material is exposed. Thus, the rate of decrease in the amount of luminescence, or quenching of luminescence of (i.e., the intensity of electromagnetic radiation emitted by) the luminescable material, corresponds to the amount of $O_2$ (e.g., fraction or concentration of a gas mixture) to which the luminescing material has been exposed.

When luminescence quenching techniques are utilized with mainstream airway adapters, such as the techniques described above with respect to mainstream infrared gas analyzers, the luminescing material is located within the airway adapter and may be positioned adjacent to or otherwise exposed through an optical window thereof. Accordingly, the material of the window must transmit radiation of at least a wavelength that is appropriate for exciting the luminescing material and a wavelength that is quenched by an analyzed material with sufficient efficiency to provide an accurate determination of an amount of the analyzed material.

The rate at which luminescence quenching occurs when a luminescing material is exposed to an analyzed material is a strong function of the temperature of the luminescing material and, thus, of a film or other substrate upon which the luminescing material is carried. It is, therefore, desirable to either control or compensate for any variation in the temperature of the carrying substrate.

Typically, the respired gases that enter a breathing circuit are approximately at body temperature and contain a substantial amount of humidity. One problem that has arisen in the use of conventional gas sensors is the gathering of moisture on the optical windows creating condensation or fogging thereon. Such fogging or condensation creates an obstacle to the transmission of the appropriate wavelengths of the electromagnetic spectrum and, thus, may result in inaccurate measurements.

To alleviate this problem, moisture (e.g., water vapor) typically is removed from respiratory gases in sidestream sampling by way of water traps or the like, formed of moisture-absorbing materials such as NAFION®, a material which includes hydrophilic regions. In mainstream gas sensors, on the other hand, the optical windows typically are heated to prevent moisture from gathering thereon.

The optical windows of mainstream gas sensors typically are heated by way of heaters associated therewith. By way of example, a heater may comprise a block of aluminum that communicates with a thermal capacitor or other electrical heating element to receive heat therefrom. A conventional heater may be associated with an edge of the optical window or placed in proximity to the window. To avoid blocking the optical path through the window, such a heater must heat a window indirectly. As a consequence of indirectly heating the portion of an optical window through which measurements are to be obtained, it is difficult to control the temperature of that portion of the window, as well as to monitor and quickly adjust the window temperature, if necessary.

Accordingly, a heating technique that provides heat directly to an element of an optical gas sensing apparatus (e.g., an optical window) without significantly compromising the optical properties of the optical gas sensing apparatus would be advantageous.

SUMMARY OF THE INVENTION

The present invention includes a heater that may be used on a window of an optical gas sensor. The heater may be substantially transparent to one or more wavelengths of electromagnetic radiation, such as those that are used in infrared monitoring of respiratory gases, anesthetic agents, or the like, or to the relevant wavelengths of electromagnetic radiation that are used to excite a particular luminescing material or that are emitted thereby.

As an example, the heater may include a heating element formed from an electrically or thermally conductive material. In addition, the material of the heating element has a high transmissivity for one or more wavelengths of electromagnetic radiation that are to be employed in an optical sensing technique appropriate for analyzing (i.e., sufficient to facilitate accurate measurement of) a particular gaseous or vaporized material. The transmissivity of the heating element for these wavelengths of radiation is preferably sufficient to provide a measurement that may be used to accurately determine the amount of the analyzed material in a sample.

A heater according to the present invention may also include a temperature-conducting element. The temperature-conducting element may communicate with the heating element or with a structure heated by the heating element. Thus, the temperature-conducting element facilitates monitoring of the temperature of the portion of the heating element or other structure with which it is in communication. Similar to the heating element, the temperature-conducting element may be formed from an electrically or thermally conductive material. If desired, the material of the temperature-conducting element also may have a high transmissivity for the one or more wavelengths of electromagnetic radiation that are to be employed in the optical sensing technique. However, the temperature-conducting element need not be positioned along an optical path of the one or more wavelengths of electromagnetic radiation and, thus, the temperature-conducting element may or may not be substantially transparent to the relevant wavelengths.

In another embodiment, the material of the heating element itself may form the window of the optical gas sensor. Accordingly, the optical window may be formed from an electrically or thermally conductive material that has a high transmissivity for one or more wavelengths of electromagnetic radiation that are to be utilized in the optical sensing technique of interest.

In yet another embodiment, a substantially unobstructed optical pathway through the window of a gas sensor may be provided by a configuration of the heating element. For instance, the heating element may be a continuous element of a configuration that substantially approximates the configuration of the outer periphery of the window, yet is of smaller dimensions than the outer periphery of the window and provides a substantially unobstructed optical pathway through the center portion of the window and the heating element. Alternatively, the heating element may be comprised of a plurality of element portions that functions together to transmit energy to the window. For example, the heating element may be comprised of two L-shaped portions or C-shaped portions positioned such that the apices or center portions, respectively, thereof are located near opposing portions of the window. The heating element may be formed from an electrically and thermally conductive material. However, as the heating element need not be positioned along an optical path of one or more wavelengths of electromagnetic radiation, the material of the heating element may or may not be substantially transparent.

Gas sensors that include a heater incorporating teachings of the present invention also are within the scope of the present invention. By way of example only, the heater may be used on any type of optical gas sensor, including, without limitation, on sensors that employ infrared and luminescence quenching monitoring techniques.

Other features and advantages of the present invention will become apparent to those of ordinary skill in the art through a consideration of the ensuing description, the accompanying drawings, and the appended claims.

BRIEF DESCRIPTION OF THE DRAWINGS

In the drawings, which illustrate exemplary embodiments of a heater and gas sensor apparatus that incorporate teachings of the present invention, and in which like reference numerals refer to like parts in the various views.

DETAILED DESCRIPTION OF THE INVENTION

Figure 1:
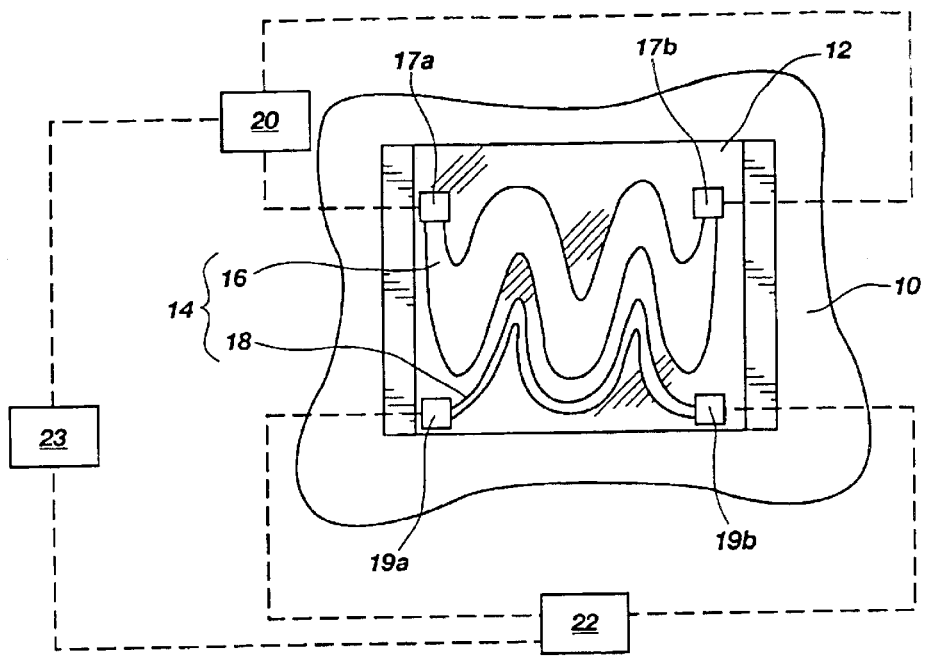
FIG. 1 is a plan view of an optical window, illustrating a heating element and temperature-conducting element thereon.

With reference to FIG. 1, a window 12 of an optical gas sensor 10 is illustrated. A heater 14, which includes a heating element 16, is positioned over a portion of window 12, including over an optical path therethrough, which, in FIG. 1, is transverse to the plane of the page. Heater 14 also includes a temperature-conducting element 18 that extends over a portion of window 12. It will be understood by those of ordinary skill in the relevant art that heating element 16 may be utilized with or without temperature-conducting element 18.

Heating element 16 may be formed from a substantially transparent conductive material, such as a conductive metal oxide (e.g., tin oxide, indium tin oxide (ITO), antimony tin oxide (ATO), zinc oxide, indium zinc oxide (IZO), etc.), cadmium sulfide, zinc oxyfluoride, platinum wire, or the like. Heating element 16 may have a resistance and a thickness that may be controlled as known to those of skill in the relevant art such that the heating element 16 may adequately heat the desired portion or portions of window 12. Further, heating element 16 may have a transmissivity sufficient to allow light to pass therethrough such that accurate measurements may be taken. Such is also known to those of skill in the art.

As used herein, "substantially transparent" refers to the ability of a conductive material to transmit one or more wavelengths of electromagnetic radiation that are used in a particular optical gas sensing technique (e.g., infrared sensing or luminescence quenching) to a degree that facilitates an accurate determination of the amount of particular gaseous or vaporized materials (e.g., $O_2$, $CO_2$, $N_2O$, an anesthetic agent, etc.) in a sample. Accordingly, for a conductive material to be "substantially transparent," it need not be completely transparent to the relevant wavelengths of the electromagnetic radiation. For luminescence-based gas analysis, exemplary conductive materials that may be used to form heating element 16 include, without limitation, ITO and ATO. Both ITO and ATO have transmittances exceeding 80% in the relevant visible light and near-infrared regions of the electromagnetic spectrum. Similarly, when infrared sensing techniques are used, exemplary materials of heating element 16 have sufficient transparency to, or transmissivity for, the one or more wavelengths of infrared radiation that are appropriate for analyzing one or more gaseous or vaporized materials of interest.

Heating element 16 may be an elongate member with a nonlinear configuration, such as the alternating serpentine configuration illustrated in FIG. 1. This nonlinear configuration of heating element 16, along with a substantially uniform width of heating element 16, facilitates the controlled delivery of a desired amount of heat to window 12 and/or any other structure adjacent to heating element 16. Alternatively, heating element 16 may comprise a substantially linear member.

Electrical terminals 17a and 17b are positioned along heating element 16 (and are shown at or near opposite ends thereof) so that heating element 16 may communicate with a source 20 of an electrical current. As an electrical current is supplied to heating element 16 through terminals 17a and 17b, heating element 16 generates heat, the amount of which depends, at least in part, on the resistivity of the substantially transparent conductive material of heating element 16. By way of example, ITO can be formed to have a resistivity of from about one ohm per square centimeter ($\Omega/cm^2$) to about 2,000 $\Omega/cm^2$. During formation, the resistivity of ITO can be controlled to within about 5% of a desired value. The temperature of heating element 16 and, thus, of the substrate with which element 16 is associated also may be varied by changing the amount of electrical current applied thereto by source 20.

Temperature-conducting element 18 also may be an elongate member with a nonlinear configuration, such as the alternating serpentine configuration shown in FIG. 1. As depicted, temperature-conducting element 18 is positioned proximate to heating element 16, but does not contact the heating element. Nonetheless, temperature-conducting element 18 is in thermal communication with a portion of window 12 that is heated by heating element 16. Terminals 19a and 19b are positioned along the length of temperature-conducting element 18 (and are shown at or near opposing ends thereof) to facilitate communication between temperature-conducting element 18 and a temperature-measuring component 22, such as a thermocouple, thermistor, or a temperature-sensing semiconductor device, such as those available from National Semiconductor Corporation of Santa Clara, Calif. Temperature-measuring component 22 may be positioned remotely from window 12, as depicted, or on or near window 12.

Temperature-conducting element 18 and temperature-measuring component 22 may have a resistance and a thickness that may be controlled as known to those of skill in the relevant art such that the temperature-conducting element 18 and the temperature-measuring component 22 may adequately conduct and measure, respectively, the temperature of the desired portion or portions of window 12. Further, temperature-conducting element 18 and temperature-measuring component 22 may have a transmissivity sufficient to allow light to pass therethrough such that accurate measurements may be taken. Such is also known to those of skill in the art.

Heating element 16 and temperature-conducting element 18 both may be formed by depositing the substantially transparent conductive material thereof. By way of example, the substantially transparent conductive material of heating element 16 and/or temperature-conducting element 18 may be deposited by physical vapor deposition techniques (e.g., radiofrequency (rf) sputtering, magnetron sputtering, direct current (dc) sputtering, reactive ion beam (RIB) sputtering, etc.). These processes may be used to form a heating element 16 and/or temperature-conducting element 18 on a wide range of substrate materials, including, without limitation, quartz, sapphire, glass, and plastics. If the substantially transparent conductive material is deposited, known patterning techniques, such as those employed in semiconductor device fabrication processes (e.g., use of a photomask and suitable etchant), may be used to pattern the deposited layer of conductive material to form a heating element 16 and/or temperature-conducting element 18 of desired configuration.

Alternatively, heating element 16 and temperature-conducting element 18 may comprise preformed structures that are positioned upon and secured to window 12. As yet another alternative, the substantially transparent conductive material of heating element 16 may form window 12 or a portion thereof.

In another embodiment, a substantially unobstructed optical pathway through a window of an optical gas sensor may be provided by a configuration of a heater positioned over only a portion of the window. By way of example, a heater, which includes a heating element, may be of a configuration that substantially approximates the configuration of an outer periphery of the window, yet is of smaller dimensions than the outer periphery of the window and provides a substantially unobstructed optical pathway through at least a center portion of the heating element.

Figure 5:
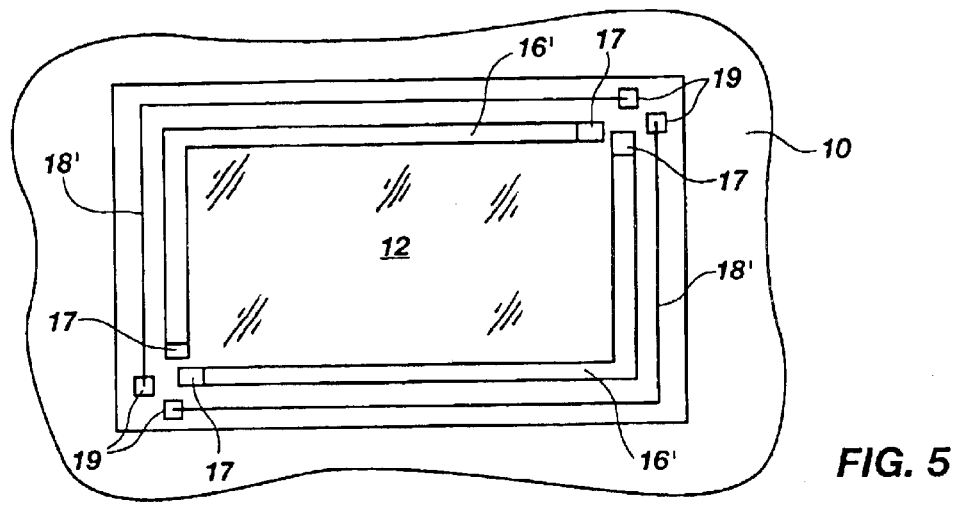
FIG. 5 is a plan view of an optical window having a heating element and temperature-conducting element thereon in accordance with an alternative embodiment of the present invention.
Figure 6:
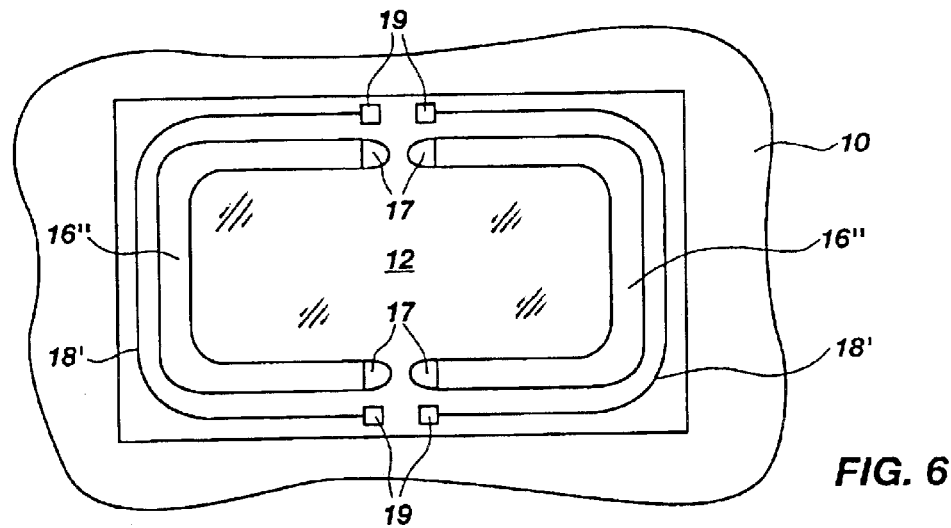
FIG. 6 is a plan view of an optical window having a heating element and temperature-conducting element thereon of yet another alternative configuration.
Figure 7:
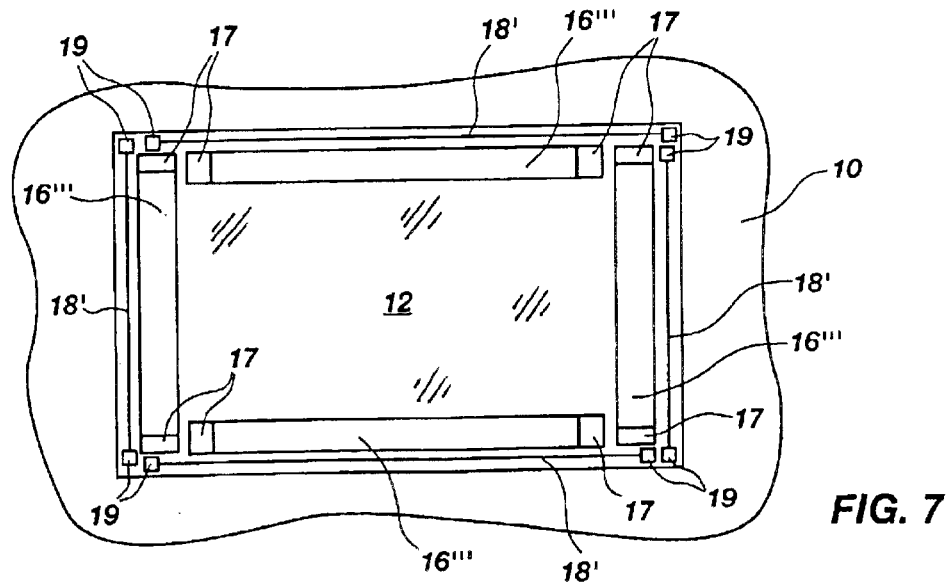
FIG. 7 is a plan view of an optical window having a heating element and temperature-conducting element of still another alternative configuration.

Alternatively, the heating element may be comprised of a plurality of element portions that function together to transmit energy to the carrying substrate of the window. For instance, referring to FIG. 5, heating element 16 may be comprised of two L-shaped portions 16' positioned such that the respective apexes of the portions are located near diagonally opposing portions of window 12. In another configuration, heating element 16 may be comprised of two opposing C-shaped portions 16" positioned such that the center portions thereof are located near opposing sides of window 12, as illustrated in FIG. 6, and the mouths of the "Cs" facing the center portion of window 12. In yet another embodiment, heating element 16 may comprise a plurality of substantially linear element portions 16''', as shown in FIG. 7. Each element portion 16''' substantially approximates a perimeter dimension of window 12, as shown.

As the heating elements are placed directly on a portion of the window rather than at an outer edge thereof or merely in proximity thereto, in contrast with prior art devices, the temperature of the portion of the window through which the optical pathway extends may be adequately monitored or controlled.

Those skilled in the art will understand and appreciate that any number of heating element configurations may be utilized to form the heater configurations of the present invention so long as an unobstructed optical pathway is provided that extends through window 12. In each of the embodiments of heating elements depicted in FIGS. 5–7, the optical pathway extends through a substantially centrally located portion of the heating element. However, configurations of heating elements also may be utilized in which the optical pathway is outside of the center portion, for instance, above or below the center portion of such a heating element. All such alternative configurations are contemplated to be within the scope of the present invention.

In an embodiment of a heating element which provides a substantially unobstructed optical pathway through the window of an optical gas sensor, the material from which the heating element is formed may or may not be transparent as the heating element is not positioned along an optical path of one or more wavelengths of electromagnetic radiation. Accordingly, the heating element may be formed from any electrically or thermally conductive material, such as gold, aluminum, or any other conductive material known in the art.

As with the substantially transparent heating elements described above, heating elements 16 providing an optical pathway due to the configuration thereof include electrical terminals 17 positioned so that heating element 16 may communicate with a source 20 of electrical current. As electrical current is supplied to heating element 16 through terminals 17, the resistance provided by heating element 16 generates heat, the amount of which depends, at least in part, on the electrical resistivity of the material of the heating element. The temperature of the heating element 16 and, thus, of a substrate, such as window 12, with which heating element 16 is associated also may be changed by varying the amount of electrical current applied thereto by a source of electrical current (not shown).

If desired, heaters that provide an optical pathway due to the configuration of the heating elements thereof may also include a temperature-conducting element 18 that extends over a portion of window 12 in proximity to heating element 16 and in thermal communication with heating element 16, wherein a portion of window 12 is heated by heating element 16. One or more temperature-conducting elements are shown in each of FIGS. 5–7. Terminals 19 are positioned along the length of temperature-conducting element 18 to facilitate communication between temperature-conducting element 18 (and are shown at or near opposing ends of each portion 18) and a temperature-measuring component (not shown), such as a thermocouple or temperature-sensing semiconductor device.

As with the substantially transparent heating elements described above, heating element 16 and temperature-conducting element 18 both may be formed on the desired substrate (including, without limitation, quartz, sapphire, glass, and plastics) by deposition techniques known in the art, e.g., by physical vapor deposition techniques. Alternatively, heating element 16 and temperature-conducting element 18 may comprise preformed structures that are positioned upon and secured to window 12.

In any of the above-described embodiments, terminals 17, 19 may be formed from any suitable, electrically conductive material and by known processes. By way of example, terminals 17, 19 may be formed from the same material as and concurrently with the formation of their respective heating element 16 or temperature-conducting element 18. Alternatively, terminals 17, 19 may be formed from a different material than that from which their respective heating element 16 or temperature-conducting element 18 is formed.

Figures 2, 3:
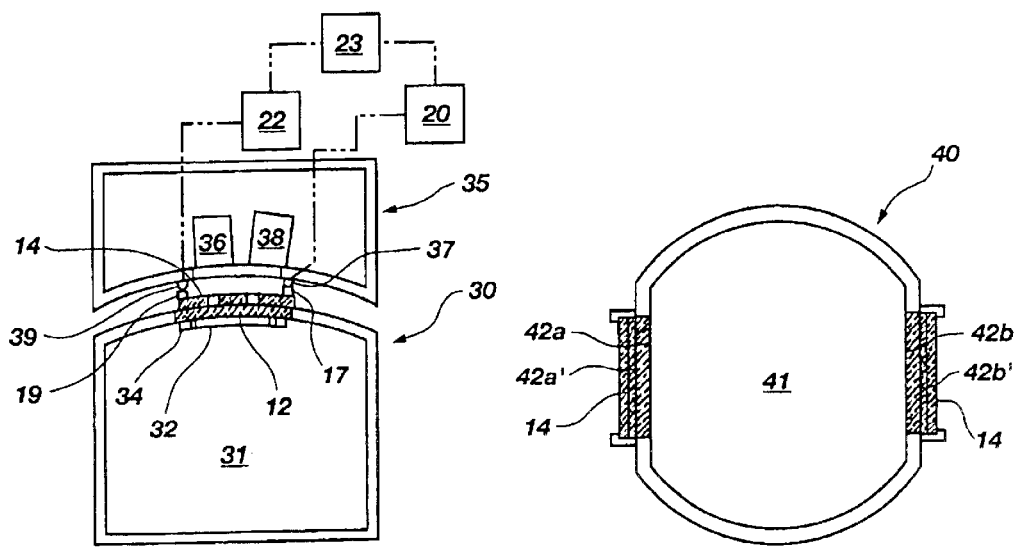
FIG. 2 is a cross-sectional representation of a first type of gas sensor assembly, depicting a heater on an optical window of the sensor.
FIG. 3 is a partial cross-sectional representation of a second type of gas sensor, depicting a heater on opposed optical windows of the sensor.

Turning now to FIG. 2, a portion of an optical gas sensor 30 is depicted that employs luminescence quenching techniques, such as those described in U.S. application Ser. No. 09/128,897, filed on Aug. 4, 1998, U.S. application Ser. No. 09/128,918, filed on Aug. 4, 1998, now U.S. Pat. No. 6,325,978, issued Dec. 4, 2002, and U.S. application Ser. No. 09/769,015, filed on Jan. 24, 2001, the disclosures of each of which are hereby incorporated herein in their entireties by this reference. Optical gas sensor 30 includes a window 12 upon which a heater 14 is positioned. As window 12 may have a nonplanar surface, such as the curved surface shown, heating element 16 (FIGS. 1 and/or 5–7) and temperature-conducting element 18 (FIGS. 1 and/or 5–7), if any, may also be nonplanar. Accordingly, if either heating element 16 or temperature-conducting element 18 comprises a preformed member, the conductive material thereof may be somewhat flexible to facilitate conformation of heating element 16 or temperature-conducting element 18 to the surface of window 12. Intimate contact between heating element 16 and window 12 may conserve power and provide for better control of the temperature of window 12 and structures adjacent thereto.

Optical gas sensor 30 also includes a substrate 32 and a quantity of luminescing material 34 carried by substrate 32 that are exposed to a sample flow path 31 and through window 12 to facilitate analysis of one or more gaseous or vaporized materials by way of luminescence quenching techniques. The exemplary positioning of heating element 16 on window 12 facilitates the more direct heating of substrate 32 and, thus, of luminescing material 34 thereon to a desired temperature. As heating element 16 is located over substrate 32, factors that would otherwise vary the temperature of substrate 32 and luminescing material 34 thereon, such as the cooling effect of gases flowing past substrate 32 and luminescing material 34, may have reduced influence on the temperatures of substrate 32 and luminescing material 34. In addition, the location of heating element 16 over substrate 32 may provide improved control over the temperatures of substrate 32 and luminescing material 34 than would more remotely positioned heaters.

Further control over the temperatures of substrate 32 and luminescing material 34 may be provided by the location of temperature-conducting element 18 over window 12, as such positioning of temperature-conducting element 18 may provide an accurate indication of the temperature of substrate 32 and, thus, of luminescing material 34 thereon. The amount of heat provided to window 12 by heating element 16 may be adjusted (i.e., increased or decreased) in response to the temperature measured by way of a thermocouple, temperature-sensing semiconductor device, thermistor, or other temperature-measuring component 22 in communication with temperature-conducting element 18. Such control may be provided by way of a control element 23 of a known type, such as a processor or smaller group of logic circuits.

As shown in FIG. 2, a transducer 35 that is configured to be assembled with optical gas sensor 30 carries a source 36 of at least one wavelength of electromagnetic radiation that excites luminescing material 34 (i.e., excitation radiation) and a radiation detector 38, which detects at least one wavelength of electromagnetic radiation emitted by luminescing material 34 (i.e., emitted radiation). Source 36 and radiation detector 38 are carried by transducer 35 such that when transducer 35 and optical gas sensor 30 are placed in an assembled relationship, source 36 and radiation detector 38 are positioned on an opposite side of window 12 from luminescing material 34, which is positioned to be exposed to a sample.

Transducer 35 also may include first electrical contacts 37 that communicate with electrical source 20 and, if optical gas sensor 30 includes a temperature-conducting element 18, second electrical contacts 39 that communicate with temperature-measuring component 22. Contacts 37 and 39 are positioned on transducer 35 so as to contact corresponding terminals 17 and 19, respectively, upon placement of optical gas sensor 30 and transducer 35 in the assembled relationship thereof. When an electrical connection between contacts 37 and terminals 17 is established, electrical power from source 20 may be supplied through transducer 3S to heating element 16. Similarly, an electrical connection between contacts 39 and terminals 19 facilitates the communication of signals (e.g., heat, electrical signals, etc.) from temperature-conducting element 18 to temperature-measuring component 22. The lack of an appropriate electrical connection between any of contacts 37, 39 and its corresponding terminal 17, 19 may cause heater 14 not to work and may also indicate that source 36 and radiation detector 38 are not properly aligned with window 12. Accordingly, a processor or less complex group of logic circuits (not shown) with which the various electronic components of transducer 35 communicate may be programmed (either by software or firmware) to generate a signal that optical gas sensor 30 and transducer 35 are not properly assembled.

As the excitation radiation and the emitted radiation pass through window 12, each also may have to pass through heating element 16. If so, the material of heating element 16 is substantially transparent to the excitation radiation, as well as to at least one wavelength of the electromagnetic radiation that is emitted by luminescing material 34 and quenched to a degree that is indicative of an amount of an analyzed substance to which luminescing material 34 has been exposed. If heater 14 includes a temperature-conducting element 18 through which one or both of the excitation radiation and emitted radiation may be transmitted, the material of temperature-conducting element 18 may also be substantially transparent to these wavelengths of electromagnetic radiation. It will be understood by those of skill in the art that if a substantially unobstructed optical pathway is provided by the configuration of heating element 16 (and temperature-conducting element 18, if desired), the material of the heating element (and temperature-conducting element) may be formed of any electrically and thermally conductive material, whether or not the material is substantially transparent.

Window 12 may be fixed to a body of optical gas sensor 30 or removable therefrom and replaceable thereon (e.g., by way of a suitable connector, such as an elastomeric connector that will adequately seal a flow path 31 through optical gas sensor 30), along with a heater 14 and luminescing material 34—carrying substrate 32 secured thereto. Alternatively, if substantially transparent, the material of heating element 16 may form window 12 or a portion thereof.

Figure 8A:
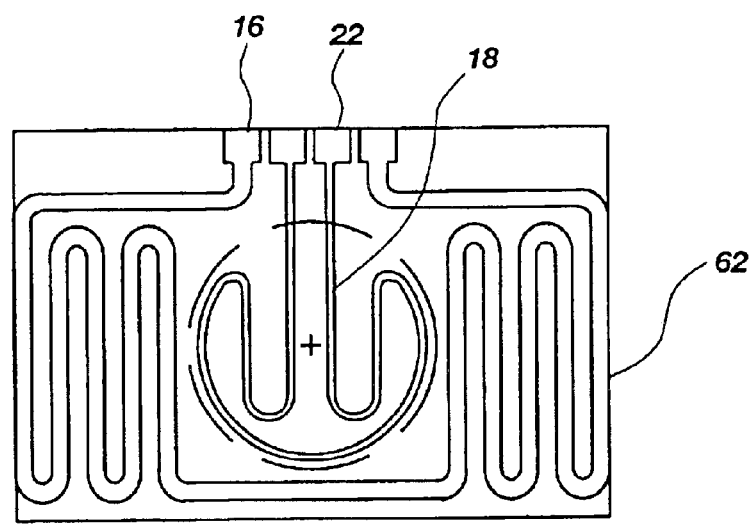
FIG. 8A is a plan view of yet another alternative configuration wherein a heating element and temperature-conducting component are carried on a window that may be secured to an optical gas sensor over and adjacent to a window thereof.
Figure 8B:
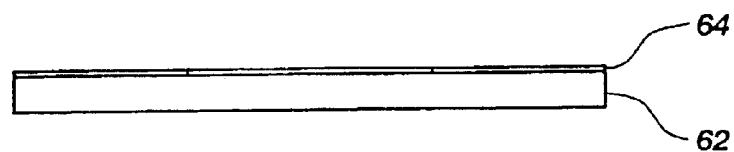
FIG. 8B is a top view of the window of FIG. 8A showing a protective cover over the temperature-measuring component thereof.

As yet another alternative, a window 62 carrying a heater 14 may be secured to optical gas sensor 30 over and adjacent to window 12. An exemplary window 62 is shown in FIGS. 8A and 8B. The window 62 may be formed of, without limitation, optical glass, fused quartz and the like. As shown in FIG. 8A, the heating element 16 and, if desired, the temperature-conducting element 18 may be formed on the bottom surface of the window while the temperature-measuring component 22 may be formed on the top surface thereof. If desired, a protective cover 64, e.g., a polycarbonate cover, may be formed on or positioned and secured to window 62 by the use of a suitable adhesive or the like, over the temperature-measuring element as shown in FIG. 8B. The heating element 16 and the temperature-conducting element 18 may be formed on the window 62 by deposition techniques known in the art, e.g., by physical vapor deposition techniques. Alternatively, heating element 16 and temperature-conducting element 18 may comprise preformed structures that are positioned upon and secured to the window 62. The heating element 16 and temperature-conducting element 18 may be formed on the window 62 or may be a separate structure to be secured thereto.

Referring now to FIG. 3, another embodiment of optical gas sensor 40 is shown. Optical gas sensor 40 is useful when infrared sensing techniques are employed and includes a sample flow passage 41 and windows 42a and 42b positioned on opposite sides of sample flow passage 41. Each window 42a, 42b may include a heater 14 thereon, which includes a heating element 16 (FIGS. 1 and/or 5–7) and may also include a temperature-conducting element 18 (FIGS. 1 and/or 5–7).

If heater 14 is positioned such that one or more wavelengths of electromagnetic radiation that will be used in sensing an amount of one or more gaseous or vaporized materials in a sample may pass through either heating element 16 or temperature-conducting element 18, the material of one or both of these elements may be substantially transparent to the relevant sensing wavelength or wavelengths of radiation that will pass therethrough.

When infrared sensing techniques are used, heater 14 is particularly suitable for preventing the buildup of moisture on, or "fogging" of, windows 42a and 42b.

As with window 12 of optical gas sensor 30, windows 42a and 42b of optical gas sensor 40 may be fixed to a body thereof or removable therefrom and replaceable thereon (e.g., by way of a suitable connector, such as an elastomeric connector that will adequately seal a flow path 41 through optical gas sensor 40). Alternatively, secondary windows 42a', 42b' carrying a heater 14 may be secured to optical gas sensor 40 over windows 42a and 42b. As yet another alternative, if substantially transparent, the material of heating element 16 may form windows 42a and 42b or a portion thereof.

Figure 4:
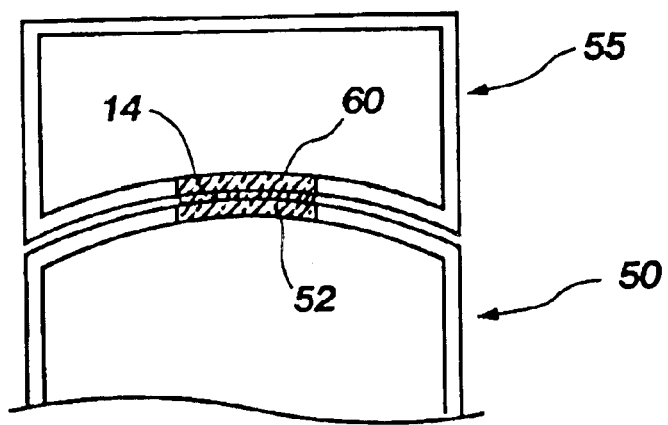
FIG. 4 is a cross-sectional representation of another embodiment of a gas sensor assembly, in which a heater is carried by a transducer component in a location that positions the heater adjacent a window of a gas sensor upon placement of the transducer and gas sensor in an assembled relationship.

In another embodiment, shown in FIG. 4, heater 14 may be carried by a transducer 55 rather than by a window 52 of an optical gas sensor 50. Heater 14, including a heating element 16 (FIGS. 1 and/or 5–7) and, optionally, a temperature-conducting element 18 (FIGS. 1 and/or 5–7), may be carried upon a heater support 60. If positioned such that one or more wavelengths of electromagnetic radiation that may be used in sensing an amount of one or more gaseous or vaporized materials in a sample will pass through, heater support 60 preferably is substantially transparent to these wavelengths, such that sufficient amounts of both excitation radiation and emitted radiation may pass therethrough. Heater support 60 may comprise a somewhat rigid member or, if it is desired that heater 14 contact and conform to the shape of a window 52 having a nonplanar surface, heater support 60 and heater 14 may be somewhat flexible. Alternatively, heater 14 may be secured to transducer 55 without a heater support 60.

Upon assembly of transducer 55 with a complementary optical gas sensor 50, heater 14 is positioned against, or in close proximity to, a window 52 of optical gas sensor 50 and, thus, heating element 16 may readily heat the same to a desired temperature.

Of course, when heater 14 is carried by transducer 55 rather than by optical gas sensor 50, heater 14 may be reused and the manufacturing costs of optical gas sensor 50 accordingly reduced. Similarly, preformed structures and secondary windows as described herein may be utilized with existing optical gas sensors, obviating the need for remanufacture and, thus, reducing costs.

Although the foregoing description contains many specifics, these should not be construed as limiting the scope of the present invention, but merely as providing illustrations of some exemplary embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions, and modifications to the invention, as disclosed herein, which fall within the meaning and scope of the claims are to be embraced thereby.

What is claimed is:

1. A heater for use on an optical gas sensor, comprising: a heating element that is substantially transparent to at least one wavelength of electromagnetic radiation to be used in an optical sensing technique for measurement of at least one gaseous or vaporized material, the heating element configured to be positioned across an optical path of the optical gas sensor without being directly secured to the optical gas sensor.

2. The heater of claim 1, wherein the optical gas sensor comprises an infrared sensor.

3. The heater of claim 1, wherein the optical gas sensor comprises a luminescence quenching sensor.

4. The heater of claim 1, wherein the gaseous or vaporized material comprises at least one of $O_2$, $CO_2$, $N_2O$ and an anesthetic agent.

5. The heater of claim 1, wherein the heating element comprises an elongate member.

6. The heater of claim 5, wherein the elongate member has a substantially nonlinear configuration.

7. The heater of claim 6, wherein the substantially nonlinear configuration of the elongate member comprises a serpentine configuration.

8. The heater of claim 5, wherein the elongate member is substantially linear.

9. The heater of claim 1, wherein the heating element comprises at least one of a conductive metal oxide, candium sulfide and zinc oxyfluoride.

10. The heater of claim 9, wherein the heating element comprises a conductive metal oxide, and wherein the conductive metal oxide comprises at least one of tin oxide, indium tin oxide, antimony tin oxide, zinc oxide and indium zinc oxide.

11. The heater of claim 1, further comprising a temperature-conducting element.

12. The heater of claim 11, wherein the temperature-conducting element is in at least thermal communication with the heating element.

13. The heater of claim 11, wherein the temperature-conducting element comprises an elongate member.

14. The heater of claim 13, wherein the elongate member has a substantially nonlinear configuration.

15. The heater of claim 14, wherein the substantially nonlinear configuration of the elongate member comprises a serpentine configuration.

16. The heater of claim 13, wherein the elongate member is substantially linear.

17. The heater of claim 13, wherein a configuration of the elongate member of the temperature-conducting element substantially approximates a configuration of the beating element.

18. The heater of claim 11, further comprising a temperature-measuring component in communication with the temperature-conducting element.

19. The heater of claim 18, wherein the temperature-measuring component comprises a thermocouple or a temperature-sensing semiconductor device.

20. The heater of claim 1, further comprising a temperature-control element in communication with the heating element.

21. A heater for use on an optical gas sensor including at least one window comprising:
   a heating element positioned over at least a portion of the at least one window of the optical gas sensor without being secured directly thereto, the heating element comprising transparent material positioned across an optical path of the optical gas sensor to provide a substantially unobstructed optical pathway through the at least one window.

22. The heater of claim 21, wherein the configuration of the heating element substantially approximates an outer periphery of the at least one window and has smaller dimensions than the outer periphery, and wherein the substantially unobstructed optical pathway is through a center of the heating element.

23. The heater of claim 21, wherein the heating element comprises at least a first element portion and a second element portion, and wherein the first and second element portions are in at least thermal communication with each other.

24. The heater of claim 23, wherein the first element portion and the second element portion are substantially L-shaped.

25. The heater of claim 23, wherein the first element portion and the second element portion are substantially C-shaped.

26. The heater of claim 21, wherein the heating element comprises a plurality of element portions.

27. The heater of claim 26, wherein each element portion of the plurality of element portions substantially approximates a dimension of a corresponding portion of an outer periphery of the at least one window.

28. The heater of claim 21, further comprising a temperature-conducting element.

29. The heater of claim 28, wherein the temperature-conducting element is in at least thermal communication with the heating element.

30. The heater of claim 28, wherein the heating element comprises a plurality of heating element portions forming a first configuration and the temperature-conducting element comprises a plurality of temperature-conducting element portions forming a second configuration, and wherein the second configuration substantially approximates the first configuration.

31. The heater of claim 28, further comprising a temperature-measuring component in communication with the temperature-conducting element.

32. The heater of claim 31, wherein the temperature-measuring component is a thermocouple or a temperature-sensing semiconductor device.

33. The heater of claim 21, further comprising a temperature-control element in communication with the heating element.

34. An optical gas sensor, comprising:
   a body defining a respiratory sample flow path therethrough, the respiratory sample flow path comprising a portion of a mainstream breathing circuit configured to communicate with an airway of an individual;
   at least one window in the body; and
   a heating element over at least a portion of the at least one window.

35. The optical gas sensor of claim 34, wherein the heating element is substantially transparent to at least one wavelength of electromagnetic radiation to be used in an optical sensing technique that facilitates measurement of at least one gaseous or vaporized material.

36. The optical gas sensor of claim 34, wherein the heating element comprises an elongate member.

37. The optical gas sensor of claim 36, wherein the elongate member comprises a flexible, substantially transparent member.

38. The optical gas sensor of claim 34, further comprising a temperature-conducting element over at least a portion of the at least one window.

39. The optical gas sensor of claim 38, wherein the temperature-conducting element comprises an elongate member.

40. The optical gas sensor of claim 39, wherein the elongate member comprises a flexible, substantially transparent member.

41. The optical gas sensor of claim 39, wherein the elongate member of the temperature-conducting element substantially approximates a configuration of the heating element.

42. The optical gas sensor of claim 34, wherein the heating element is coupled to a transducer, the transducer being positioned in proximity 10 the at least one window upon assembly of the transducer with the body.

43. The optical gas sensor of claim 42, wherein the heating element is substantially aligned with at least a portion of the at least one window upon assembly of the transducer with the body.

44. The optical gas sensor of claim 43, wherein the heating element at least partially conforms to a shape of a surface of at least the portion of the at least one window upon assembly of the transducer with the body.

45. The optical gas sensor of claim 34, wherein the heating element has a configuration that permits a substantially unobstructed optical pathway through the at least one window.

46. The optical gas sensor of claim 45, wherein the configuration of the heating element substantially approximates a configuration of an outer periphery of the at least one window and has smaller dimensions than the outer periphery, and wherein the substantially unobstructed optical pathway is through a center of the heating element.

47. The optical gas sensor of claim 45, wherein the heating element comprises a plurality of element portions.

48. The optical gas sensor of claim 47, wherein each element portion substantially approximates at least one dimension of a corresponding portion of an outer periphery of the at least one window.

49. The optical gas sensor of claim 45, further comprising a temperature-conducting element.

50. The optical gas sensor of claim 49, wherein the temperature-conducting element is in at least thermal communication with the heating element.

51. The optical gas sensor of claim 49, wherein the heating element comprises a plurality of heating element portions forming a first configuration and the temperature-conducting element comprises a plurality of temperature-conducting element portions forming a second configuration, and wherein the second configuration substantially approximates the first configuration.

52. The optical gas sensor of claim 49, further comprising a temperature-measuring component in communication with the temperature-conducting element.

53. A transducer for use in an optical sensing technique for measuring at least one gaseous or vaporized material, the transducer comprising:

a transducer body configured to be removably secured to an optical gas sensor; and a heating element that is substantially transparent to al least one wavelength of electromagnetic radiation coupled to the transducer body.

54. The transducer of claim 53, wherein upon assembly of the transducer with an optical gas sensor having at least one window therein, the heating element is positioned in proximity to the at least one window.

55. The transducer of claim 54, wherein the heating element is substantially aligned with at least a portion of the at least one window upon assembly of the transducer with the optical gas sensor.

56. A transducer for use in an optical sensing technique for measuring at least one gaseous or vaporized material, the transducer comprising:

a transducer body configured to be removably secured to an optical gas sensor; and a heating element coupled to the transducer body, the heating element having a configuration that permits a substantially unobstructed optical pathway through at least one window of the optical gas sensor upon assembly of the transducer with the optical gas sensor.

57. The transducer of claim 56, wherein the heating element is substantially aligned with at least a portion of the at least one window upon assembly of the transducer with the optical gas sensor.

58. A method of heating an optical window of a gas sensor comprising:

providing an optical gas sensor having a body that defines a sample flow path therethrough, with the sample flow path being positioned along a mainstream breathing circuit that communicates with an airway of an individual, the body having at least one window therein, the optical gas sensor also including a heating element over at least a portion of the at least one window, the heating element being coupled to a source of electrical power;

introducing or sensing radiation through the heating element on the at least one window; and supplying power to the heating element to heat the at least one window.

59. The method of claim 58, further comprising:

sensing a temperature of the at least one window.

60. The method of claim 59, further comprising:

varying an amount of power supplied to the heating element responsive to a sensed temperature.

61. The method of claim 58, further comprising:

contacting the at least one window with a transparent heating element that is separate therefrom.

62. The method of claim 58, wherein providing comprises positioning the heating element in close proximity to but out of contact with the at least one window.

* * * * *